(12) United States Patent
Velasquez

(10) Patent No.: US 6,198,398 B1
(45) Date of Patent: Mar. 6, 2001

(54) SOIL MOISTURE MONITORING DEVICE

(76) Inventor: Evelyn Velasquez, 401 Richmond Dr. #219, Millbrae, CA (US) 94030

( * ) Notice: Subject to any disclaimer, the term of this patent is extended or adjusted under 35 U.S.C. 154(b) by 0 days.

(21) Appl. No.: 09/563,198

(22) Filed: May 2, 2000

(51) Int. Cl.[7] .................................................. G08B 21/00
(52) U.S. Cl. .................. 340/604; 340/691.6; 340/693.5; 47/79; 73/73; 324/696
(58) Field of Search ..................................... 340/602, 604, 340/618, 620, 691.6, 693.5, 331; 73/73; 324/694, 696; 47/79

(56) References Cited

U.S. PATENT DOCUMENTS

| | | | |
|---|---|---|---|
| 3,916,678 | * 11/1975 | Lohoff | 47/79 |
| 4,020,417 | * 4/1977 | Brehob et al. | 340/602 |
| 4,130,012 | * 12/1978 | Lockerby et al. | 73/73 |
| 4,184,445 | * 1/1980 | Burrows | 73/73 |
| 4,931,775 | * 6/1990 | Sheriff | 340/604 |
| 5,428,348 | * 6/1995 | Gault | 340/618 |

* cited by examiner

Primary Examiner—Daniel J. Wu
(74) Attorney, Agent, or Firm—Goldstein & Canino

(57) ABSTRACT

A moisture monitoring device, for use in monitoring the soil moisture level of a potted plant, comprising a tubular housing having a proximal end and a distal end. A moisture sensor is located at the distal end, which is ordinarily submerged within the soil of the potted plant. An indicating LED is located at the proximal end, which is normally visible above the soil of the potted plant. A blinker circuit is located within the housing and is capable of controlling illumination of the indicating LED. The moisture sensor modulates the blinker circuit such that as the soil moisture level decreases, the blinker circuit causes the indicating LED to flash more rapidly.

5 Claims, 3 Drawing Sheets

US 6,198,398 B1

SOIL MOISTURE MONITORING DEVICE

BACKGROUND OF THE INVENTION

The invention relates to soil moisture monitoring device. More particularly, the invention relates to a device which warns a caretaker that a plant requires watering, and further indicates when the plant is in grave need of watering.

It is well known that in order for plants to survive, they need water. In particular, the soil in which they are planted must remain moist. Failure to provide the plant with adequate moisture will effect the lifespan of the plant, and will prevent it from reaching its potential. The most intuitive way to keep the soil moist is to water the plant periodically. However, the frequency of watering required to keep the soil moist varies with the environment in which the plant is growing. The soil moisture content can even vary between two potted plants positioned right alongside each other. Accordingly, the plant caretaker must continually manually check the soil of each plant to see if it is in need of watering.

Automatic plant watering devices are available to automate the task of plant watering. However, these devices typically work using timers. Since the soil moisture can depend on so many factors, including atmospheric temperature and humidity, it is usually difficult to predict what an appropriate watering interval will be. Accordingly, such an automatic plant watering system would usually end up watering the plant either too frequently or too infrequently.

Several devices have been proposed which indicate the adequacy or inadequacy of soil moisture. For Example, U.S. Pat. No. 4,020,417 to Behob et al.; U.S. Pat. No. 3,916,678 to Lohoff; U.S. Pat. No. 3,951,098 to Meyer; U.S. Pat. No. 4,184,445 to Burrows and U.S. Pat. No. 4,931,775 to Sheriff all disclose different systems which indicate when the soil is too dry and/or too moist. However, these devices fail to warn the caretaker of the severity of the situation.

While these units may be suitable for the particular purpose employed, or for general use, they would not be as suitable for the purposes of the present invention as disclosed hereafter.

SUMMARY OF THE INVENTION

It is an object of the invention to produce a device for monitoring the soil of a plant which indicates to a caretaker when the plant needs to be watered. Accordingly, the invention senses a low moisture condition in the soil, and provides indication by means of a flashing light upon presence of such a condition.

It is another object of the invention to provide a device for monitoring the soil of a plant which indicates how severely the plant needs to be watered. Accordingly, as the soil becomes progressively dryer, the indicating light flashes more rapidly.

It is a further object of the invention to provide a device for monitoring the soil which is self-contained, so that it may be easily installed in a potted plant, or conveniently moved between several potted plants for measuring or monitoring the moisture level of several such plants.

The invention is a moisture monitoring device, for use in monitoring the soil moisture level of a potted plant, comprising a tubular housing having a proximal end and a distal end. A moisture sensor is located at the distal end, which is ordinarily submerged within the soil of the potted plant. An indicating LED is located at the proximal end, which is normally visible above the soil of the potted plant. A blinker circuit is located within the housing and is capable of controlling illumination of the indicating LED. The moisture sensor modulates the blinker circuit such that as the soil moisture level decreases, the blinker circuit causes the indicating LED to flash more rapidly.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
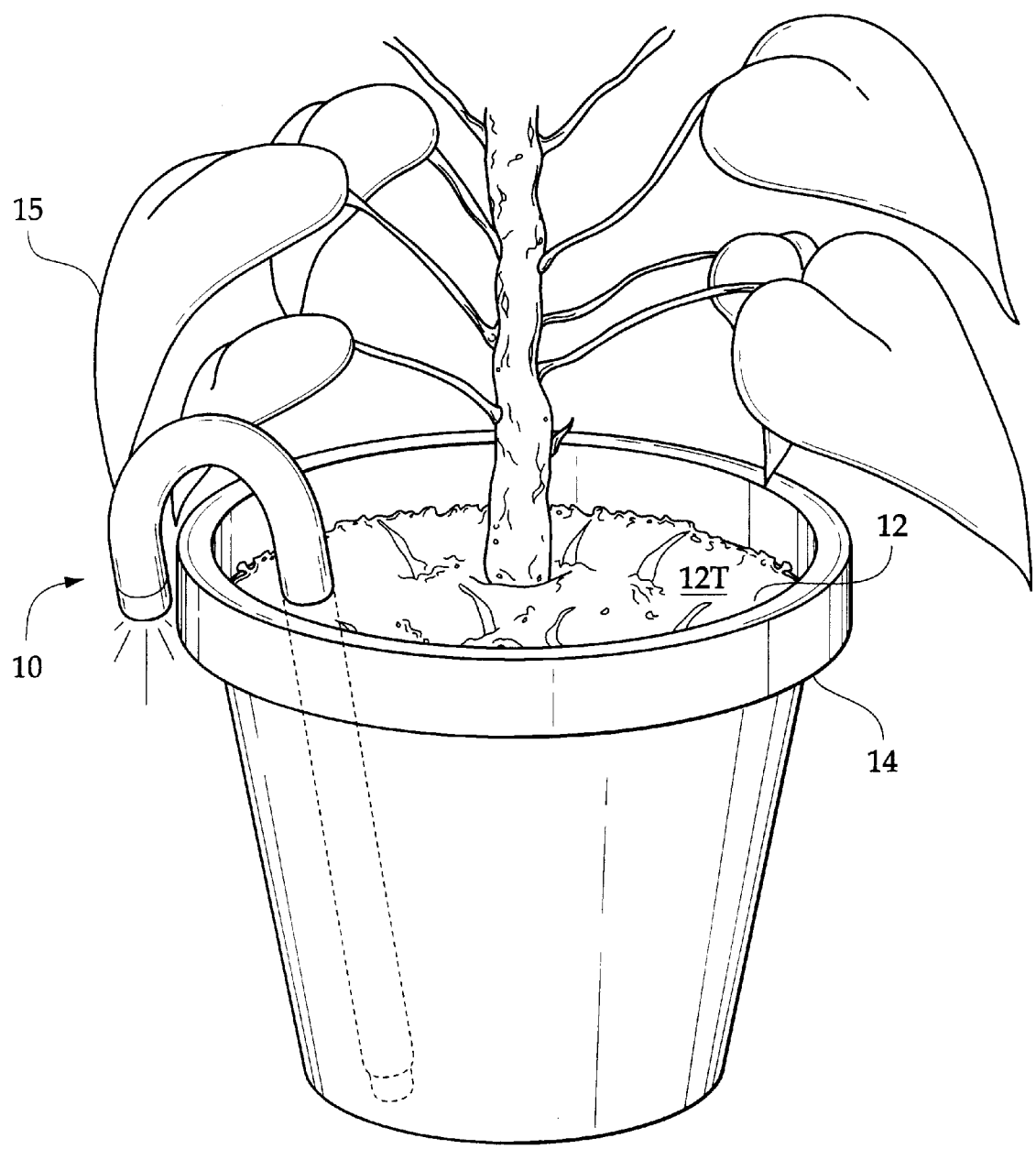
FIG. 1 is a diagrammatic perspective, showing an embodiment of the invention inserted into the soil of a potted plant.

FIG. 1 illustrates a device for monitoring the soil of a plant and indicating when the plant needs to be watered 10, which is referred to hereinafter simply as a monitoring device 10. The monitoring device 10 is shown in use, located within soil 12 has a soil top level 12T, which is contained within a pot 14. A plant 15 is potted within the pot 14. The soil 12 has a moisture level, which will vary continually from moist, to dry, to very dry. As illustrated in FIG. 1, the monitoring device 10 is illuminated, indicating a dry moisture level within the soil 12.

Figure 2:
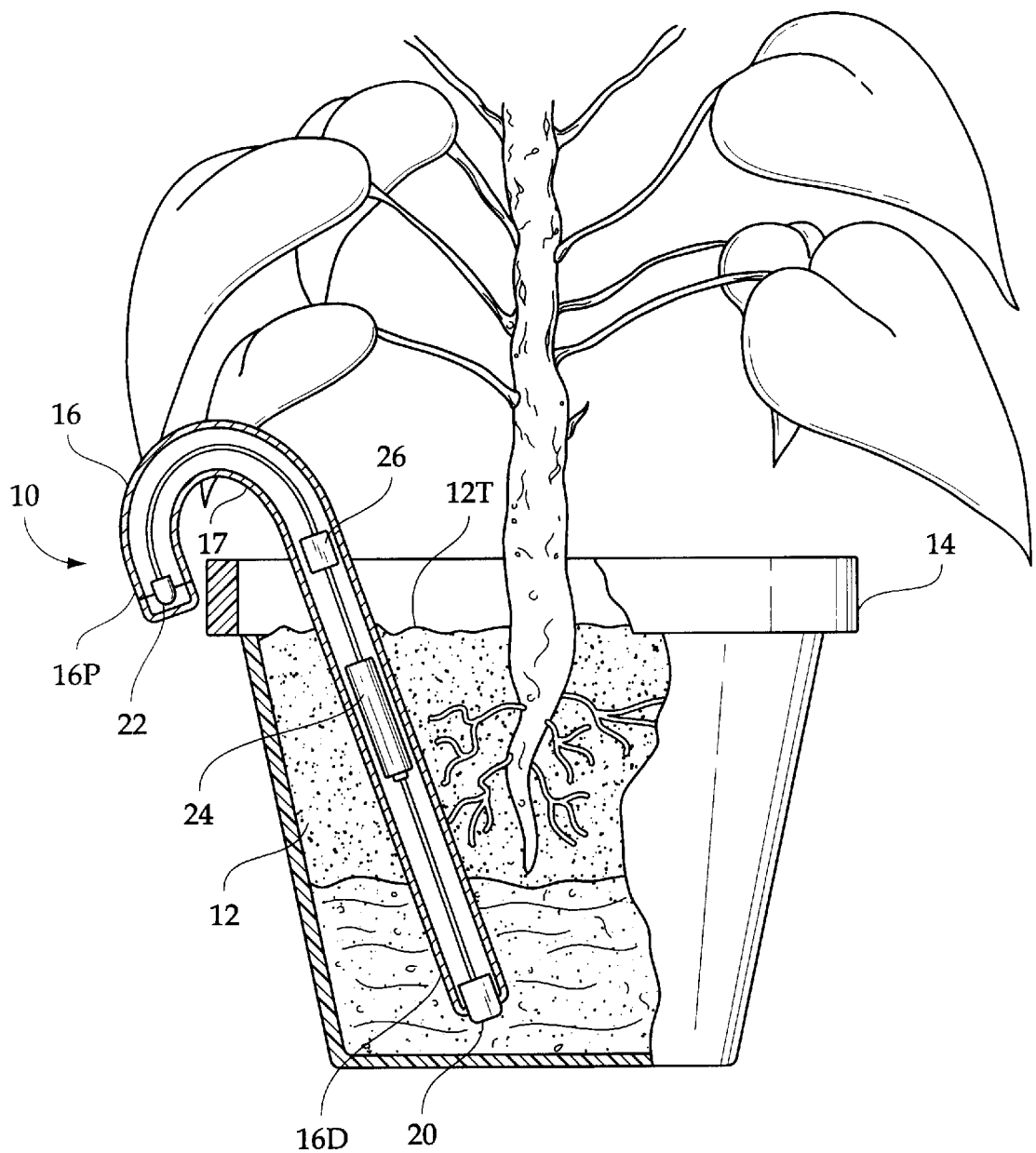
FIG. 2 is a side elevational view, with parts broken away, illustrating various components of the invention contained within the housing thereof.

FIG. 2 illustrates the monitoring device 10, located within a pot 14, wherein both the pot 14 and the monitoring device 10 have been broken away to reveal details thereof. In particular, the monitoring device 10 has a tubular housing 16 having a proximal end 16P and a distal end 16D. During ordinary use, the distal end 16D is submerged within the soil 12, and the proximal end 16P remains in view, above the soil top level 12T.

The tubular housing 16 may be substantially straight between the proximal end 16P and distal end 16D, or cane shaped as illustrated in FIG. 2, having a hook 17 near the proximal end 16P. A moisture sensor 20 is located at the distal end 16D, which is capable of sensing varying degrees of moisture. Typically, the moisture sensor 20 is a resistor which varies in resistance with different moisture levels. An indicating LED 22 is located at the proximal end 16P. The indicating LED 22 is capable of producing visible light, and is suitable for the purposes of the present invention because of its low power consumption characteristics. Power to illuminate the indicating LED 22 is supplied by a battery 24, although other power sources, including solar power, may be used to power the device 10. Preferably though, the battery 24 is located within the tubular housing 16 between the proximal end 16P and distal end 16D, and should be situated so that it is easily replaceable.

In accordance with the present invention then, when the moisture sensor 20 detects a low moisture level, the indicating LED 22 is illuminated with power supplied by the battery 24. However, a blinker circuit 26 is interposed therebetween, so that the indicating LED 22 will not simply illuminate, but will flash at a flashing interval. In addition, the flashing interval will become more rapid as the soil moisture level that is perceived by the moisture sensor 20 decreases.

Thus, when the soil 12 becomes dry, the indicating LED 22 will flash until the plant is watered and a low moisture condition is no longer detected by the moisture sensor 20. However, if the plant is not watered, the indicating LED 22 will flash more rapidly, increasingly the likelihood that the flashing light 22 will be noticed by a caretaker, who will then proceed to water the plant.

Figure 3:
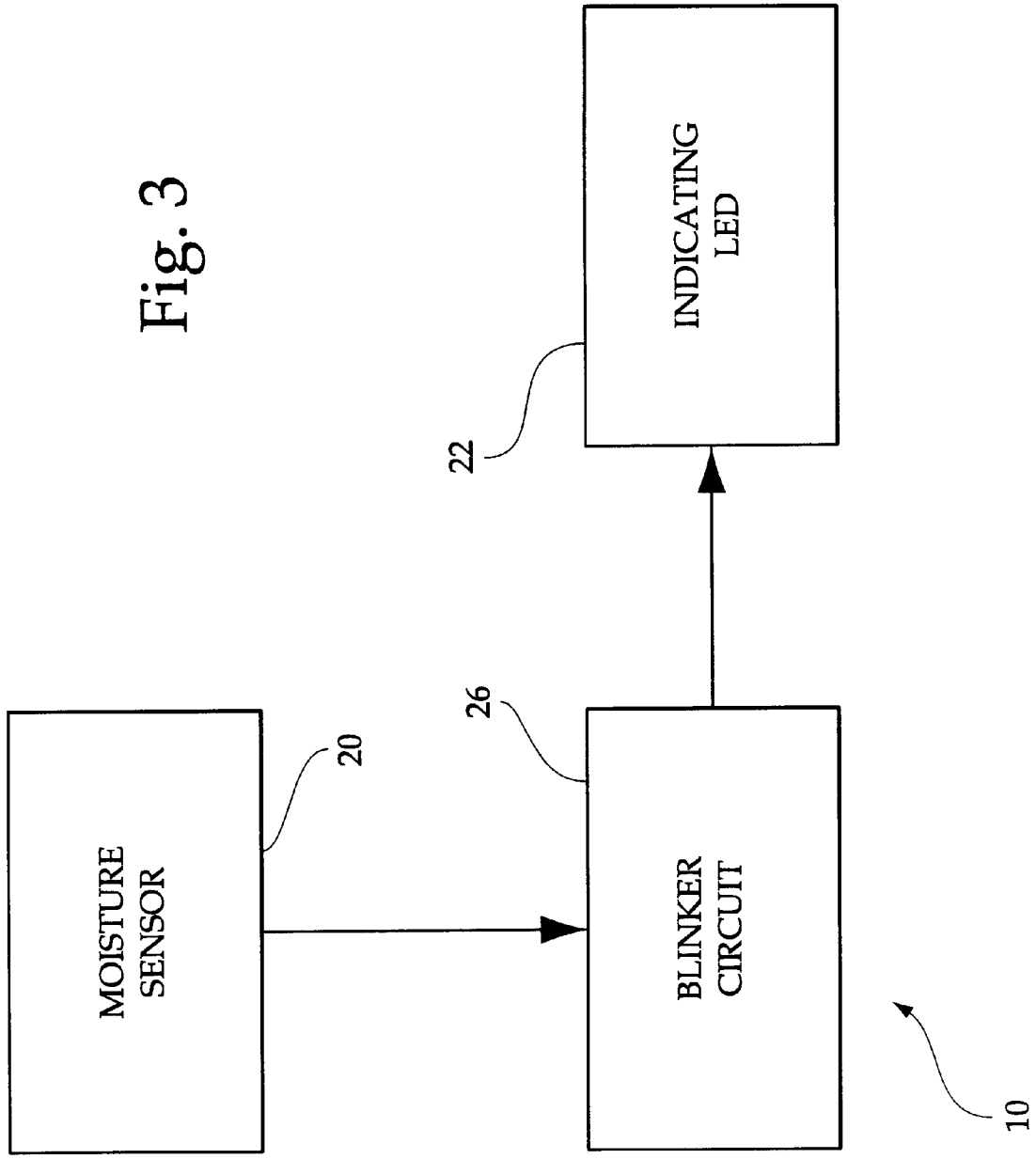
FIG. 3 is a block diagram, illustrating the interconnection of major functional components of the invention.

FIG. 3 is a block diagram, illustrating interconnection of major functional components of the monitoring device 10. In particular, the blinker circuit 26 controls illumination of the indicating LED 22. In addition, the blinker circuit 26 is modulated by the moisture sensor 20, such that lower moisture levels will cause the blinker circuit 26 to flash the indicating LED 22 more rapidly.

In conclusion, herein is presented a system for monitoring the moisture level in the soil of a potted plant, wherein a caretaker is notified by means of a flashing indicator when the moisture level necessitates that the plant be watered. In addition, as the moisture level continues to drop, the indicating LED will flash more rapidly.

What is claimed is:

1. A moisture monitoring device, for use with a plant, planted in soil located within a pot, the soil having a moisture level, comprising:

a tubular housing, having a proximal end and a distal end, the distal end submergible within the soil during ordinary usage, the proximal end visible above the soil during ordinary usage;

a moisture sensor located at the distal end of the tubular housing, the moisture sensor capable of detecting the moisture level of the soil in varying degrees;

an indicating LED located at the proximal end of the tubular housing, the indicating LED capable of illuminating to indicate to a caretaker that the plant should be watered; and a blinker circuit, the blinker circuit controlling the illumination of the indicating LED such that the blinker circuit causes the indicating LED to flash at a flashing interval, the moisture sensor modulating the blinker circuit such that the lower the moisture level in the soil, the more rapid the flashing interval.

2. A moisture monitoring device, for use with a plant, planted in soil located within a pot, the soil having a moisture level, comprising:

a housing;

a moisture sensor, the moisture sensor capable of detecting the moisture level of the soil in varying degrees;

an indicating means capable of illuminating to indicate to a caretaker that the plant should be watered; and a blinker circuit, the blinker circuit controlling the illumination of the indicating means such that the blinker circuit causes the indicating means to flash at a flashing interval, the moisture sensor modulating the blinker circuit such that the lower the moisture level in the soil, the more rapid the flashing interval.

3. The moisture monitoring device as recited in claim 2, wherein the housing has a proximal end and a distal end, the distal end submergible within the soil during ordinary usage, and the proximal end visible above the soil during ordinary usage.

4. The moisture monitoring device as recited in claim 3, wherein the moisture sensor is located at the distal end, the indicating means located at the proximal end.

5. A plant moisture monitoring method, for use with a potted plant which is potted in soil, for monitoring a soil moisture level of the soil, using a monitoring device having a proximal end and a distal end, the proximal end having an indicating LED, the distal end having a moisture sensor, comprising the steps of:

submerging the monitoring device within the soil such that the distal end is located within the soil and the proximal end is visible above the soil;

detecting the moisture level of the soil with the moisture sensor;

flashing the indicating LED when the detected moisture level of the soil is low; and increasing the rate of flashing as the detected moisture level decreases.

\* \* \* \* \*